US011298004B2

(12) United States Patent
Ostrovsky et al.

(10) Patent No.: US 11,298,004 B2
(45) Date of Patent: Apr. 12, 2022

(54) ENDOSCOPE TIP ACCESSORY DEVICE WITH DIMENSION VARIABILITY COMPENSATION

(71) Applicant: HOYA Corporation, Tokyo (JP)

(72) Inventors: Isaac Ostrovsky, Wellesley, MA (US); Azadeh Khanicheh, Somerville, MA (US); Hrishikesh Vishvas Deo, Brooklyn, NY (US)

(73) Assignee: Hoya Corporation, Tokyo (JP)

( * ) Notice: Subject to any disclaimer, the term of this patent is extended or adjusted under 35 U.S.C. 154(b) by 485 days.

(21) Appl. No.: 15/907,530

(22) Filed: Feb. 28, 2018

(65) Prior Publication Data

US 2019/0261835 A1  Aug. 29, 2019

(51) Int. Cl.
*A61B 1/00* (2006.01)
*A61B 1/005* (2006.01)
*A61M 25/00* (2006.01)

(52) U.S. Cl.
CPC .......... *A61B 1/00131* (2013.01); *A61B 1/005* (2013.01); *A61B 1/0014* (2013.01); *A61B 1/00064* (2013.01); *A61B 1/00112* (2013.01); *A61B 1/00137* (2013.01); *A61M 2025/0096* (2013.01)

(58) Field of Classification Search
CPC ............ A61B 1/00089; A61B 1/00101; A61B 1/00135; A61B 1/00154
USPC .................................................. 600/121–122
See application file for complete search history.

(56) References Cited

U.S. PATENT DOCUMENTS

| | | | |
|---|---|---|---|
| 2005/0245942 A1* | 11/2005 | DiPoto ............... | A61B 17/7007 606/108 |
| 2015/0148606 A1* | 5/2015 | Rottenberg ........ | A61B 1/00101 600/114 |
| 2017/0112365 A1 | 4/2017 | Ostrovsky et al. | |
| 2018/0153380 A1* | 6/2018 | Rottenberg .............. | A61B 1/01 |

(Continued)

FOREIGN PATENT DOCUMENTS

| | | |
|---|---|---|
| JP | 2003-339631 A | 12/2003 |
| WO | WO 2018/194138 A1 | 10/2018 |

OTHER PUBLICATIONS

International Search Report dated Mar. 29, 2019 in International Application No. PCT/IB2018/059677 (6 pgs.).

(Continued)

*Primary Examiner* — Alexandra L Newton
(74) *Attorney, Agent, or Firm* — Finnegan, Henderson, Farabow, Garrett & Dunner LLP

(57) ABSTRACT

Embodiments of the disclosure include an endoscope accessory assembly for use on an endoscope, during procedures. The endoscope accessory assembly may comprise an accessory device comprising a first base, a plurality of flexible struts, and webbing connecting each of the flexible struts. The accessory device is configured to receive a distal end of an endoscope. The endoscope accessory assembly may further comprise a dimension-compensating component comprising a second base, a plurality of flexible arms extending radially out from the second base, and at least one chamber at a distal end of the flexible arms. The accessory device is configured to be over-molded onto the dimension-compensating component in order to form the endoscope accessory assembly.

12 Claims, 9 Drawing Sheets

(56) References Cited

U.S. PATENT DOCUMENTS

2018/0168437 A1* 6/2018 Schreiner ............ A61B 1/00128
2019/0380564 A1* 12/2019 Viala .................. A61B 1/00137

OTHER PUBLICATIONS

Written Opinion of the International Searching Authority dated Mar. 29, 2019 in International Application No. PCT/IB2018/059677 (8 pgs.).

* cited by examiner

ENDOSCOPE TIP ACCESSORY DEVICE WITH DIMENSION VARIABILITY COMPENSATION

TECHNICAL FIELD

The embodiments of the present disclosure generally relate to an endoscope accessory assembly. More particularly, the embodiments relate to a dimension-compensating component for allowing more flexibility to variations in manufacturing tolerances when the assembly is attached to a distal end of an endoscope.

BACKGROUND

In endoscopic procedures, endoscopes are inserted through an orifice or incision and through the body lumen. The endoscope may be guided through internal body lumens, e.g., the gastrointestinal tract, to a region of interest, such as the stomach, cecum, duodenum, small intestine, large intestine, or esophagus. The instruments are provided with a fiber-optic, charge-couple device (CCD), or a CMOS camera, which enable images to be transmitted along the flexible endoscopes and reproduced on a display external to the body of the patient. Accordingly, it is possible to view the internal surfaces of body lumens during these procedures. For example, a gastroscope may be used to view the internal surfaces of the esophagus, stomach, or duodenum.

Endoscopic procedures may be used to provide visual diagnosis (e.g., of an ulceration or polyp), treatment, biopsy, and/or removal of tissue. While colonoscopic and enteroscopic examinations may be effective techniques to assess the state of health of an internal body region, they may cause complications and, in some instances, may fail to allow a clinician to accurately visualize a region of interest. For example, a clinician may not be able to complete the procedure, may fail to detect a polyp, lesion, or other structure, or may cause injury to the body lumen in which the endoscope is inserted, e.g., via the application of traumatic force, which may result in inflammation, burns, bleeding, scarring, perforation, or other injury.

Endoscopic procedures may be time consuming for patients and medical personnel alike, depending upon how difficult it is to advance a scope through the body lumen or to view the surrounding region. Anatomical and technological limitations may also contribute to the difficulties of these procedures. First, the anatomy of a body lumen, e.g., the colon, may be tortuous and the lining may be uneven. For example, the colon is arranged into a series of folds. As the tip of the endoscope passes along the lumen of the colon, these folds may hamper the clinician's ability to visualize the entire surface of the mucosa and, in particular, to detect pre-malignant and malignant lesions and polyps located along these folds. For example, during endoscope withdrawal, lesions located on the distal faces of these folds may not be visualized.

Additionally, the tortuous nature of the gastrointestinal tract may make it difficult for a clinician to navigate the endoscope to the region of interest. The turns of the bowel, folded surface of the colon, and effects of gravity may cause the endoscope to bump and press on the body lumen as the endoscope is advanced or withdrawn. This may lead to stretching of the bowel, perforation, bleeding, trauma to the mucosa, inflammation, or other injury.

A number of products have attempted to address the challenges associated with endoscopic procedures. For example, active balloon endoscopes and balloon attachments have been developed. Additionally, other accessory devices configured to receive a distal end of an endoscope has been developed. However, these accessory devices rely on a certain level of interference, also referred to as an attachment force, in order to fit onto the endoscope tip and remain secured. In addition, a certain level of resistance, also called the detachment force, is needed when removing the accessory devices from the endoscope tip such that the accessory devices do not unintentionally fall off from the endoscope tip during the procedures.

The level of attachment and detachment forces, however, must be maintained within a small range of values, thereby presenting difficulties in manufacturing these types of accessory devices. For example, the attachment and detachment forces must not be excessively high such that the accessory device could be manually placed onto the endoscope tip before the procedure and manually removed after the procedure without damaging the endoscope. Especially because the outer surface of an endoscope is generally made of a thin, flexible skin, the endoscope can be rather fragile and could be easily torn. On the other hand, the attachment and detachment forces must not be excessively low such that the accessory device does not readily fall off during the procedure.

Accordingly, an improved endoscope accessory device is needed that is more compliant upon insertion and is relatively flexible to manufacturing tolerances. Such a device may allow a clinician to safely and easily attach and remove the endoscope accessory assembly without damaging the endoscope.

SUMMARY

The embodiments of the present disclosure include an improved endoscope accessory assembly. Advantageously, the exemplary embodiments provide an endoscope accessory assembly comprising an accessory device and a dimension-compensating component for facilitating easier attachment and removal of the assembly. Various embodiments of the disclosure may include one or more of the following aspects.

In accordance with one embodiment, an endoscope accessory assembly comprising an accessory device and a dimension-compensating component is provided. The accessory device may further comprise a first base having a first inner surface dimensioned to receive a distal end of an endoscope. The accessory device may further comprise a plurality of flexible struts extending radially out from the first base in a first direction. Webbing may connect each of the flexible struts and further form a collapsible umbrella. The dimension-compensating component may further comprise a second base having a second inner surface dimensioned to receive at least a portion of an outer surface of the first base. The dimension-compensating component may further comprise a plurality of flexible arms extending radially out from the second base in a second direction that is opposite the first direction. The dimension-compensating component may further comprise at least one projection extending radially inward at a distal end of the flexible arms. The accessory device may be over-molded onto the dimension-compensating component in order to form the endoscope accessory assembly.

In another embodiment, at least one of the first base or the second base may be triangular, rectangular, or cylindrical in shape such that the endoscope accessory assembly may receive an endoscope of a variety of shapes. In other aspects, the at least one projection at the distal end of the flexible arms may be configured to stop the distal end of the endoscope from extending beyond the distal end of the flexible arms.

According to another embodiment, the inner diameter at a distal end of the flexible arms of the dimension-compensating component may be less than the outer diameter of the distal end of the endoscope. When the dimension-compensating component is at rest without the endoscope engaged, the flexible arms may deform inward such that an inner diameter of the second base is greater than an inner diameter at the distal end of the flexible arms. However, when the accessory device receives the distal end of the endoscope, the plurality of flexible arms of the dimension-compensating component may deform outward and, thus, generate a force inward onto the distal end of the endoscope. The inner diameter of the first base of the accessory device may remain constant throughout.

In other embodiments, the dimension-compensating component may be made of plastic, and the accessory device may be made of silicone. In further embodiments, the accessory device may be over-molded onto the dimension-compensating component such that at least a portion of the first inner surface and a portion of the outer surface of the accessory device encapsulate the plurality of flexible arms. The first inner surface of the accessory device may further comprise at least one crush rib.

In another embodiment, the endoscope accessory assembly may further comprise an extension cup coupled to the distal end of the flexible arms of the dimension-compensating component. When the accessory device is over-molded onto the dimension-compensating component, the extension cup may extend beyond a distal end of the first base of the accessory device. The extension cup may further comprise a third base and a second plurality of flexible arms. The second plurality of flexible arms of the extension cup may be configured to couple to the distal end of the flexible arms of the dimension-compensating component. In some embodiments, a distal end of the third base of the extension cup may be tilted at an angle relative to a vertical axis.

According to another embodiment of the present disclosure, a dimension-compensating component is provided. The dimension-compensating component may comprise a base having a substantially cylindrical inner surface and a first set of flexible arms extending radially out from the base. The first set of flexible arms may further comprise a proximal end and a distal end. The proximal end may be coupled to the base and the distal end may further comprise a projection extending radially inward.

In other aspects, the base and the first set of flexible arms of the dimension-compensating component may be dimensioned to receive a distal end of an endoscope. At rest when the dimension-compensating component has not yet received an endoscope, the first set of flexible arms may deform inward such that an inner diameter of the base is greater than an inner diameter at the distal end of the arms. When the dimension-compensating component receives the endoscope, the first set of flexible arms may deform outward and generate a force inward onto the distal end of the endoscope. In some aspects, an inner diameter at a distal end of the first set of flexible arms may be less than an outer diameter of the distal end of the endoscope.

In another embodiment, the dimension-compensating component may further comprise an extension cup coupled to the distal end of the first set of flexible arms. The extension cup may further comprise a second base and a second set of flexible arms. The second set of flexible arms may be configured to couple to the distal end of the first set of flexible arms. In other embodiments, a distal end of the second base of the extension cup may be tilted at an angle relative to a vertical axis.

Additional objects and advantages of the embodiments will be set forth in part in the description that follows, and in part will be obvious from the description or may be learned by practice of the embodiments. The objects and advantages of the embodiments will be realized and attained by means of the elements and combinations particularly pointed out in the appended claims.

It is to be understood that both the foregoing general description and the following detailed description are exemplary and explanatory only and are not restrictive of the claims.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIGS. 7A-6B illustrate a tilted extension cup and a prior accessory device coupled to the tilted extension cup;

DETAILED DESCRIPTION

Reference will now be made in detail to the exemplary embodiments of the present disclosure described below and illustrated in the accompanying drawings. Wherever possible, the same reference numbers will be used throughout the drawings to refer to same or like parts.

For purposes of this disclosure, an "endoscope" may refer to any suitable type of scope for insertion into a patient during a medical procedure. Endoscopes may include, for example, colonoscopes, duodenoscopes, gastroscopes, sigmoidoscopes, enteroscopes, ureteroscopes, and bronchoscopes. The term "procedure" broadly refers to the insertion of an endoscope into a patient for any purpose, including, but not limited to, surgery, biopsy, diagnosis, treatment, visualization, implantation or removal of a device, suction, or insufflation.

Figure 1:
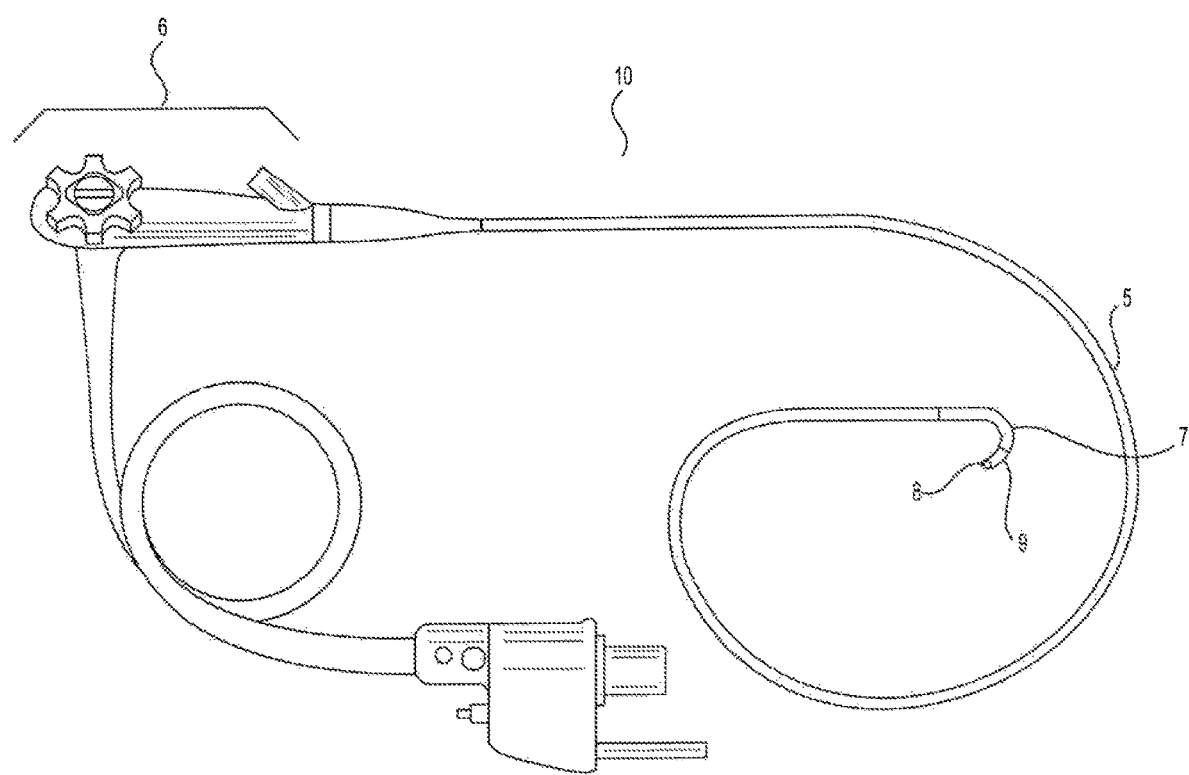
FIG. 1 illustrates an exemplary endoscope for receiving an endoscope accessory assembly.

Reference is now made to FIG. 1, which illustrates a generic endoscope device 10. The endoscope 10 may comprise an insertion tube 5, an endoscope tip 9 at a distal end, and a camera 8 housed at the end of the endoscope tip 9. The endoscope 10 may further comprise a control portion 6 at a proximal end of the endoscope device 10 that a clinician can use to maneuver the insertion tube 5 and the endoscope tip 9 inside a patient. The endoscope 10 may further comprise a bendable portion 7 that may be controlled remotely by a clinician in order to navigate the turns of a lumen. In some embodiments, the insertion tube 5 may be flexible while the endoscope tip 9 may be rigid. The insertion tube 5 may be flexible such that it can bend as the endoscope 10 is inserted into a patient.

Figure 2A:
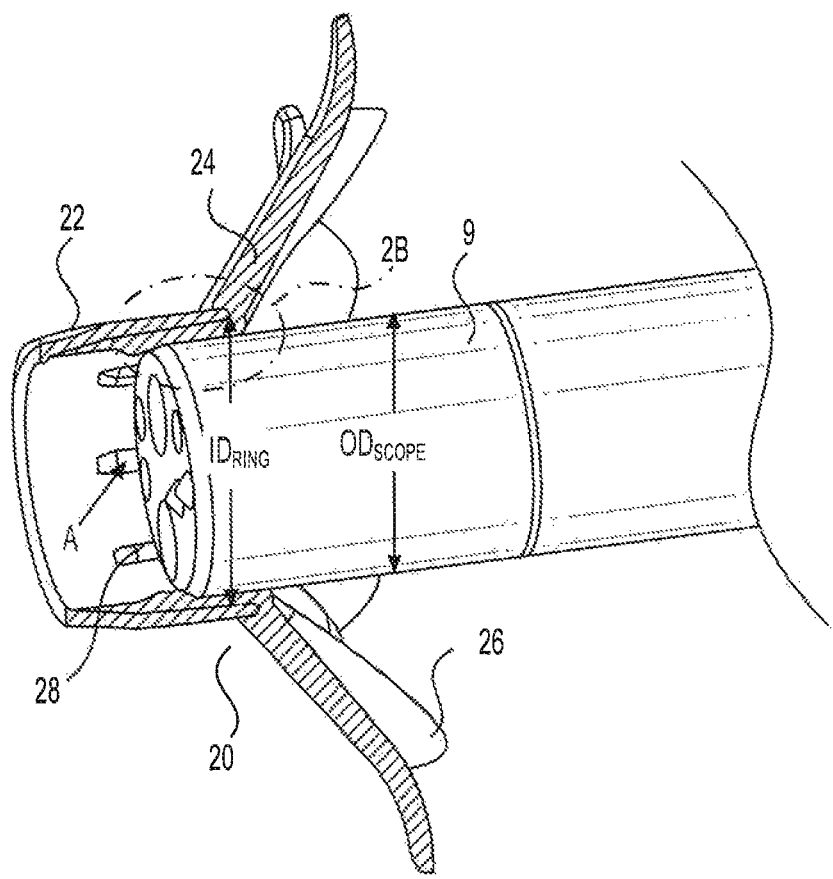
FIGS. 2A-2B illustrate a prior accessory device, in the form of an arrangement of collapsible struts for manipulating bowel folds, mounted on an endoscope tip.

Reference is now made to FIG. 2A, which illustrates a prior accessory device 20 mounted on the endoscope tip 9. The prior accessory device 20 is configured to attach to a distal end of the endoscope tip 9. The device 20 comprises a ring-shaped base 22, which is dimensioned to receive an outer surface of the endoscope tip 9. The base 22 has an inner diameter ($ID_{RING}$) that is slightly larger than an outer diameter of the endoscope tip ($OD_{SCOPE}$). In order to provide an optimal fit, the shape of the base 22 and the shape of the endoscope tip 9 are complimentary. The base 22 may be slid, twisted, or friction-fit onto the endoscope tip 9.

The accessory device 20 can take any form useful to a clinician when attached to an endoscope. In an exemplary embodiment, the accessory device 20 further comprises a plurality of flexible struts 24 extending radially out from the base 22. The flexible struts 24 may flex between different positions. For example, the struts 24 may flex in a proximal direction along the axis of the endoscope during insertion of the endoscope into the body. Once inserted into a body lumen and guided to a region of interest, the endoscope may be slowly withdrawn, and the struts 24 may engage the body lumen and flex out from the axis of the endoscope. As the endoscope is further withdrawn, the struts 24 may bend further until the tips of the struts 24 point in a distal direction.

Webbing 26 may be provided that is configured to connect each of the plurality of struts 24. The combination of the webbing 26 and the struts 24 may form a collapsible umbrella extending out from the base 22. Webbing 26 may extend all the way down the length of the struts 24 or cover only a portion of the length of the struts 24.

The ring-shaped base 22 further comprises one or more crush ribs 28. Crush ribs 28 protrude from the inner surface of the base 22 to contact the endoscope and increase interference with the base 22. Therefore, the crush ribs 28 increase sliding friction to prevent the accessory device 20 from sliding off the endoscope tip 9 during a procedure.

The crush ribs 28 may be configured to deform slightly upon engagement with the endoscope tip 9 or when pressure is applied to the accessory device 20 to remove the device 20 from the endoscope tip 9. As such, crush ribs 28 may be formed of an elastic material. However, as mentioned above, it may be difficult to manufacture the accessory device 20 such that the dimensions of the base 22 and the crush ribs 28 are within a small manufacturing tolerance to provide an optimal fit with the endoscope tip 9. In order to ensure the accessory device 20 does not easily disengage with the endoscope tip 9 and to ensure the endoscope 10 is not damaged during removal of the device 20, the attachment and detachment force would need to be between about 3 and 5 lbs. The "attachment force" and the "detachment force" herein refers to the resistance created to remove the accessory device 20 from the endoscope tip 9 due to a certain level of interference needed in order to ensure optimal fit of the device 20 onto the endoscope tip 9. As such, if the attachment and detachment force is less than about 3 lbs., the accessory device may slide off easily during an endoscopic procedure. Similarly, if the attachment and detachment force is more than about 5 lbs., it may be difficult to place the accessory device onto an endoscope and remove the device without damaging the scope.

The attachment force and the detachment force may be functions of interference between an outside diameter of the endoscope tip 9 ($OD_{SCOPE}$) and an inside diameter of the accessory device 20 ($ID_{RING}$). During manufacturing, it is inevitable that $OD_{SCOPE}$ and $ID_{RING}$ vary, thereby varying the attachment and detachment force. In order to limit the amount of variation to an acceptable range, the method of manufacturing the accessory device 20 would need to provide a narrow dimensional variation, which would make the manufacturing process quite expensive.

In order to address this problem, the crush ribs 28 were utilized to allow the attachment and detachment force to be less sensitive to dimensional variation. The crush ribs 28 allow for wider dimensional variation, thereby allowing less expensive manufacturing methods to still satisfy the acceptable range of attachment and detachment force. The height of the crush ribs 28 generally reduces the space, in which the endoscope tip 9 is supposed to fit, when the accessory device 20 is attached to the endoscope tip 9. Therefore, interference is created.

When the accessory device 20 is attached to the endoscope tip 9, the crush ribs 28 elastically deform, thereby generating a force between the accessory device 20 and the endoscope tip 9. The force generated creates the attachment and detachment force. Therefore, the greater the interference, the higher the force generated, and the smaller the interference, the lower the force generated.

Figure 2B:
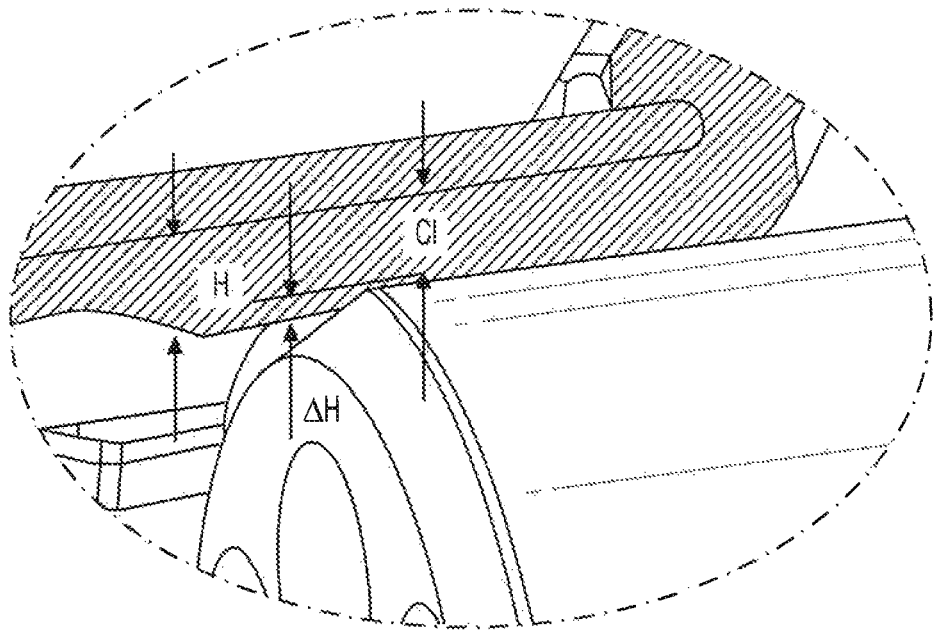

Reference is now made to FIG. 2B, which illustrates an expanded view of section "2B" of FIG. 2A. For a single elastic crush rib 28, the force generated could be modeled according to the equation below:

$$F = K \times C \times \varepsilon \times A$$

where K is the coefficient of friction;
C is the compression modulus of the material of the crush rib;
ε is the strain, or the relative deformation of the crush rib; and
A is the area of the crush rib in contact with the endoscope.

For a crush rib 28 of height H, the strain (ε) would be:

$$\varepsilon = \frac{\Delta H}{H}$$

$$\Delta H = H - Cl$$

where Cl is half of the clearance between the outer diameter of the scope and the inner diameter of the base 22 of the accessory device 20. For example, the clearance (Cl) can be indicated as:

$$Cl = \frac{ID_{RING} - OD_{SCOPE}}{2}$$

The strain (ε) could also be expressed as:

$$\varepsilon = \frac{\Delta H}{H} = \frac{(H - Cl)}{H}$$

The area of the crush rib 28 that is in contact with the endoscope tip 9 (A) would be equivalent to the area of the longitudinal projection of the crush rib 28. This area of contact (A) is not constant.

The volume of the crush rib 28 is a function of the crush rib height (H) and the area of contact (A). The volume of the crush rib 28 (V) can be expressed as:

$$V = A \times H$$

As such, when the accessory device 20 is attached to the endoscope tip 9, the crush rib 28 is compressed into the clearance (Cl) between the outer diameter of the scope tip 9 and the inner diameter of the base 22. Therefore, the actual area of contact would be:

$$A = \frac{V}{Cl} = A_0 \frac{H}{Cl}$$

where $A_0$ is the area of the crush rib that is not compressed.

Combining the equations above, the force generated by a single crush rib 28 when the accessory device 20 is attached to the endoscope tip 9 can be rewritten as:

$$F = K \times C \times \frac{H - Cl}{H} \times A_0 \times \frac{H}{Cl}; \text{ or}$$

$$F = K \times C \times (H - Cl) \times \frac{A_0}{Cl}$$

The coefficient of friction (K) and the compression modulus (C) are material properties of the crush rib 28 and, thus, these variables remain constant. If it is assumed that the initial area of the crush rib 28 ($A_0$) and the clearance (Cl) between the endoscope tip 9 and the base 22 of the accessory device 20 do not vary during the manufacturing process and remain constant, the height of the crush rib 28 (H) would be the only variable that changes within the manufacturing tolerance. Then, the attachment and detachment force would be proportion to ΔH or (H–Cl). Even though the manufacturing tolerance would be set for the height of the crush rib 28 (H), the manufacturing tolerance would affect the value of (H–Cl), which is a smaller component than the height (H). As such, the manufacturing tolerance set for the height (H) would have a greater effect on the variation of the value of ΔH or (H–Cl), and thus, the force generated, which is proportional to the value of (H–Cl).

Figure 3:
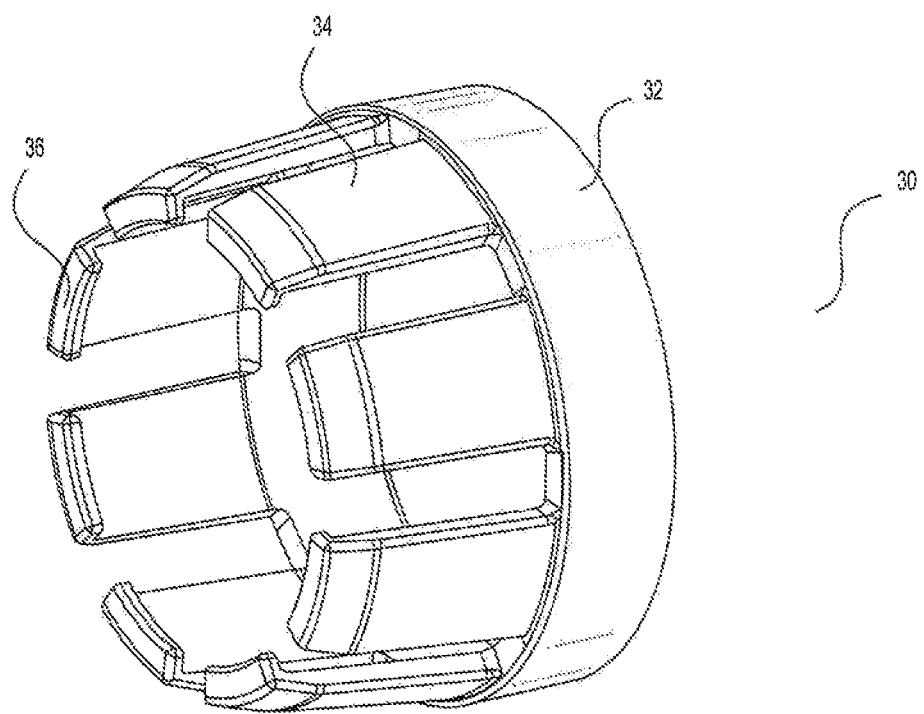
FIG. 3 illustrates an exemplary dimension-compensating component, in accordance with the embodiments of the present disclosure.

In order to reduce the effect of the manufacturing tolerance on the force generated when the accessory device is attached to the endoscope tip, an improved dimension-compensating component may be used. Reference is now made to FIG. 3, which illustrates an exemplary dimension-compensating component, in accordance with the embodiments of the present disclosure. As shown in FIG. 3, an exemplary dimension-compensating component 30 may include a base 32. The base 32 may be configured to receive at least a portion of an accessory device such that an inner surface of the base 32 contacts at least a portion of an outer surface of an accessory device. The inner surface of the base 32 may be substantially smooth. In other embodiments, the inner surface of the base 32 may comprise a textured pattern that extends across the inner surface of the base 32. For example, the inner surface may include a coating or texturing that maintains the placement of the accessory device on the dimension-compensating component 30. In some embodiments, the base 32 may be formed of a material that is rigid. For example, the base 32 may be formed of hard plastic, like for example polycarbonate. In some embodiments, the base 32 may be dimensioned to receive an endoscope tip (not shown). Therefore, an inner diameter of the base 32 may depend on the size and/or shape of an outer diameter of the endoscope tip. For example, an inner diameter of the base 32 may range from about 8 mm to 15 mm.

An outer surface of the base 32 may also be substantially smooth or it could include one or more ridges, protrusions, indents, and/or textures to assist a clinician with attaching and removing the component 30 from the endoscope tip. In other embodiment, one or more dimples (not shown) may be provided on the outer surface of the base 32 and/or an outer surface of the accessory device (not shown) in order to provide a better grip.

The dimension-compensating component 30 may further comprise a plurality of flexible arms 34. The dimension-compensating component 30 may include anywhere from about one to about twenty flexible arms 34 attached to the base 32. For example, there may be three, four, five, six, eight, or twelve flexible arms 34 attached to the base 32. The flexible arms 34 may be configured to deform between a resting position and an attachment position. At resting position, the flexible arms 34 may deform slightly inward such that an inner diameter of the base 32 is greater than an inner diameter at the distal end of the flexible arms 34. When the dimension-compensating component is configured to receive an endoscope tip (not shown) during the attachment position, the flexible arms 34 may deform outward and generate a force inward (also referred to as the attachment and detachment force) onto the endoscope tip.

In some embodiments, the flexible arms 34 may range from about 10 mm to about 70 mm. When the dimension-compensating component is configured to receive an endoscope tip, the flexible arms 34 may deform within a range from about 0.01 mm to about 3.0 mm. In some embodiments, the flexible arms 34 may deform within a range of about 0.2 mm to about 1.0 mm.

One or more projection extending radially inward 36 may be formed at a distal end of the flexible arms 34. For example, projections 36 may be provided at the distal end of every flexible arm 34. In other embodiments, projections 36 may be provided at the distal end of every other flexible arm 34. The projections 36 may extend substantially perpendicularly to the flexible arms 34. In other embodiments, the projections 36 may extend radially inward at an angle between about 75° and about 90°. The projections 36 are configured to stop the endoscope tip from extending beyond a predetermined distance when the endoscope tip is attached. For example, the projections 36 may stop the distal end of the endoscope tip from extending beyond the distal end of the flexible arms 34. Therefore, the projections 36 may prevent the outer surface of the endoscope tip from being damaged.

Figure 4:
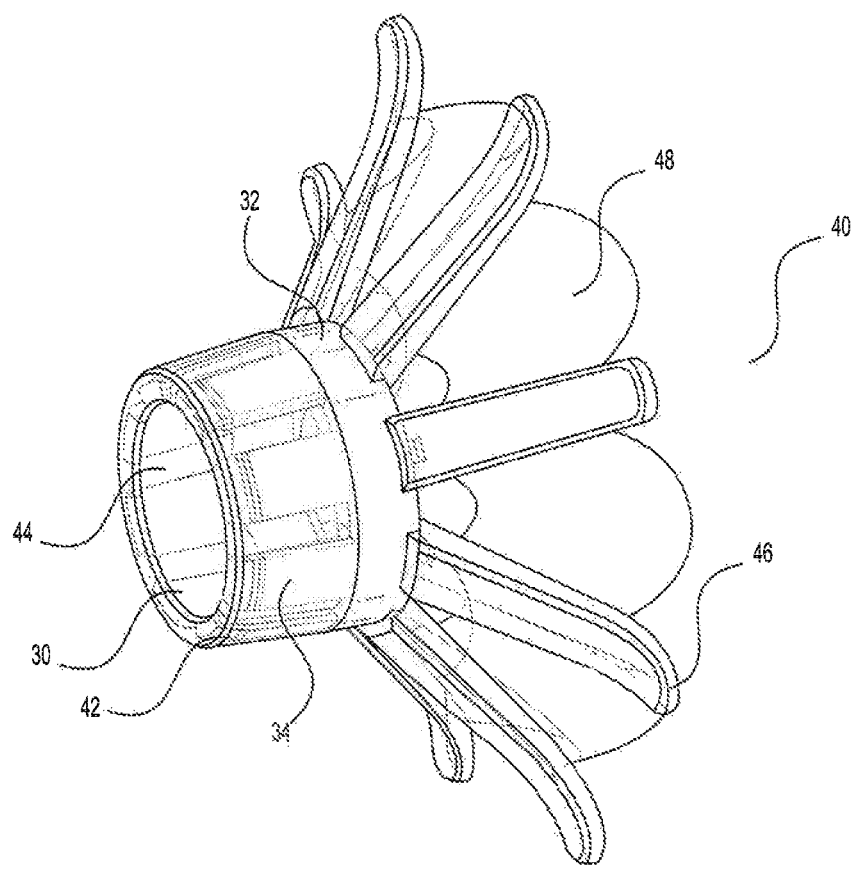
FIG. 4 illustrates an exemplary endoscope accessory assembly for receiving an endoscope, in accordance with the embodiments of the present disclosure.

Reference is now made to FIG. 4, which illustrates an exemplary endoscope accessory assembly for receiving an endoscope, in accordance with the embodiments of the present disclosure. The exemplary endoscope accessory assembly 40 may comprise the exemplary dimension-compensating component 30 and an exemplary accessory device 42, according to the embodiments of the present disclosure. Unlike the prior accessory device 20, the accessory device 42 may be over-molded onto the dimension-compensating component 30. For example, the dimension-compensating component 30 may be manufactured via injection molding, casting, extruding, or 3D printing. Then, the accessory device 42 may be over-molded onto the manufactured dimension-compensating component 30 such that the flexible arms 34 are encapsulated by a base 44 of the accessory device 42. In some embodiments, the flexible arms 34 may be encapsulated by the base 44 of the accessory device 42, while the base 32 of dimension-compensating component 30 is still exposed. Accordingly, an inner surface of the base 32 of the dimension-compensating component may receive or contact at least a portion of an outer surface of the base 44 of the accessory device 42.

In some embodiments, the accessory device 42 may comprise the base 44 and a plurality of struts 46 extending radially out from the base 44 in a first direction. The plurality of flexible arms 34 may extend radially out from the base 32 of the dimension-compensating component in a second direction, opposite the first direction. The base 44 may include a plurality of gripping elements (not shown) on an outer surface, such as gripping windows, pressure pads, dimples, protrusions, ridges, indents, and/or textures. These gripping elements may assist a clinician in attaching the endoscope accessory assembly 40 to and removing the assembly 40 from an endoscope tip (not shown).

The plurality of struts 46 may be connected to one another by webbing 48. The plurality of struts 46 may be configured to flex relative to base 44 in order to assume a more streamlined, collapsed profile upon insertion into a body lumen and an enlarged, expanded profile upon withdrawal. In the collapsed configuration, the struts 46 may be configured to fold such that they are substantially parallel to an axis of the endoscope to which the endoscope accessory assembly 40 is attached. On the other hand, in the expanded configuration, the struts 46 may be configured to extend away from the endoscope's axis and toward the periphery of the body lumen in order to gently push on the body lumen into which the endoscope is inserted. Accordingly, when expanded, the struts 46 may apply pressure to the circumference of the body lumen in order to enlarge the body lumen in the region surrounding the endoscope accessory assembly 40.

The plurality of struts 46 may extend along webbing 48, forming a surface that connects the struts 46 with one another, similar in manner to how the material of an umbrella extends between the ribs of an umbrella. Webbing 48 may extend along all or along a portion of the length of the struts 46. In some embodiments, webbing 48 may extend all the way down to the base 44 and the webbing 48 may lie flush with the tips of the struts 46. In other embodiments, webbing 48 may only cover a portion of the length of the struts 46 and may not extend all the way down to the base 44. In some embodiments, a gap may be resent in embodiments in which webbing 26 does not extend down struts 24 to meet the base 44. The gap may allow fluids and gases to pass through when endoscope accessory assembly 40 is being withdrawn from the body lumen. Webbing 48 may be formed with a soft material, such as silicone or any other suitable material, such that the webbing does not cause any tearing or injuries to the body lumen when the endoscope accessory assembly 40 is being withdrawn from inside of the patient.

By extending between the struts 46, webbing 48 distributes the force applied to the body lumen by allowing the struts 46 to extend more evenly across a larger surface area when in the expanded configuration. Instead of the struts 46 applying elevated pressure to the body lumen, which may cause trauma to the lumen, webbing 48 and struts 46 cooperatively create a continuous contact surface over which the force of expanded struts 46 is distributed along the periphery of the body lumen.

Optionally, the base 44 may further comprise one or more crush ribs (not shown). Crush ribs may protrude from the inner surface of the base 44 to contact the endoscope tip and increase contact pressure between the base 44 and the endoscope tip. Thus, the crush ribs may increase sliding friction to prevent the endoscope tip from disengaging from the endoscope during a procedure. However, because the plurality of flexible arms 34 may generate sufficient force onto the endoscope tip to prevent the endoscope tip from disengaging from the assembly 40, one or more crush ribs may not be necessary on the inner surface of the base 44.

Alternatively, an inner surface of the base 44 may be substantially smooth or may include a textured pattern that extends across the inner surface of the base 44 and may not include crush ribs. For example, the inner surface of the base 44 may include a coating or texturizing that maintains the placement of endoscope accessory assembly 40 on an endoscope tip. In some embodiments, the base 44 may be formed of a material with a higher coefficient of friction. For example, the base 44 may be formed of silicone, or any other suitable material, such that the base 44 and the endoscope accessory assembly 40 may be securely attached to the endoscope tip. In other embodiments, the base 44 may be formed of silicone in order to provide protection and cushion for the endoscope when the endoscope accessory assembly 40 is attached to the endoscope tip.

The outer surface of the base 44 may also be formed of silicone, or any other suitable material, so that, when the endoscope accessory assembly 40 is attached to the endoscope tip, silicone will cover at least a portion of the endoscope tip. Generally, an endoscope comprises sharp edges, which may cause injuries inside the patient's body lumen. Accordingly, it may be advantageous to form the outer surface of the base 44 with a soft material, such as silicone, so that the silicone covers at least a portion of the sharp edges of an endoscope. The outer surface of the base 44 may further include one or more ridges, protrusions, indents, dimples, and/or textures to assist a clinician with attaching and removing the endoscope accessory assembly 40 from an endoscope. For example, dimples may be formed around the outer perimeter of the base 44. In other embodiment, when attaching and removing the endoscope accessory assembly 40 from an endoscope tip, the clinician may be able to grab the webbing 48 of the accessory device 42 and pull the endoscope accessory assembly 40 off of the endoscope.

The overall size and shape of the base 44 may be based on the size and shape of the distal end of the endoscope tip, on which the endoscope accessory assembly 40 is configured to attach. Exemplary endoscopes may range in diameter from approximately 8.0 mm to about 15 mm. Therefore, the inner diameter of the base 44 may be dimensioned to receive a distal end of the endoscope tip. The outer diameter of the base 44 may be configured to protrude only slightly from the surface of the endoscope onto which it fits so as to not substantially increase the diameter of the endoscope tip in order to facilitate insertion when the endoscope accessory assembly 40 is attached to the endoscope tip. In addition, the outer diameter of the base 44 may depend on an inner diameter of the base 32 of the dimension-compensating component 30. For example, the outer diameter of the base 44 may be dimensioned such that, when the accessory device 42 is over-molded onto the dimension-compensating component 30, the outer diameter of the base 44 is in contact with the inner diameter of the base 32 of the dimension-compensating component 30. In other embodiments, the base 32 and/or the base 44 may come in a variety of sizes and shapes, for example, depending on the size and/or shape of the endoscope that the endoscope accessory assembly 40 is intended for use with. In some embodiments, the base 32 and/or the base 44 may be triangular, rectangular, or polygonal in shape.

In addition, the base 44 and/or the base 32 may be dimensioned so that when mounted on an endoscope, endoscope accessory assembly 40 may engage only a distal-most portion of the endoscope. The distal-most ends of many endoscopes include a rigid tip, which may be made of rigid plastic or metal, in order to define the end of the endoscope, provide rigidity, and encase/protect the optical components located on the distal face of the endoscope. The bending portion of the endoscope is generally located proximal to this distal metal ring. The bending portion of most endoscopes is more flexible and is generally made of more delicate materials. Thus, it may be easier to puncture or damage the bending portion of an endoscope. Accordingly, given the expense of endoscopes, it would be undesirable to have an endoscope accessory assembly 40 that extends into the bending portion of an endoscope, as this may damage the endoscope during use.

The plurality of struts 46 and the base 44 may form one component such that the plurality of struts 46 is affixed to the base 44. In other embodiments, the plurality of struts 46 may be individually and removably coupled to the base 44. Likewise, the plurality of flexible arms 34 may be affixed to the base 32 such that they form one component. In other embodiments, the flexible arms 34 may be manufactured separately from the base 32 and individually and removably coupled to the base 32.

The accessory device 42 of the endoscope accessory assembly 40 may comprise anywhere from about one to about twenty struts 46. For example, there may be three, four, five, six, eight, or twelve struts 46 attached to the base 44. The struts 46 may be flexible and may be configured to flex between a resting position, an insertion position, and a withdrawal position. In the resting position, as shown in FIG. 4, the struts 46 may flare out from the axis of the endoscope. The natural outward biasing of the struts 46 in the resting position may facilitate the transition between the insertion and the withdrawal position inside the body lumen. For example, in the insertion position, struts 46 are configured to flex in a proximal direction along the axis of the endoscope. This results in a streamlined profile for facilitating insertion of the endoscope into the body. Once inserted into a body lumen and guided to a region of interest, the endoscope may be slowly withdrawn to visualize the region of interest. As the endoscope is withdrawn, struts 46 may engage the body lumen and flex out from the axis of the endoscope. As the endoscope is further withdrawn, struts 46 may bend until the tips of struts 46 point in a distal direction. This is the withdrawal position.

In some embodiments, the total length of the plurality of flexible arms 34 and/or the total length of the plurality of struts 46 may range from about 5 mm to about 70 mm. In another embodiment, the total length of the plurality of flexible arms 34 and/or the total length of the plurality of struts 46 may range from about 30 mm to about 70 mm. The total length of the plurality of struts 46 may, also, vary depending on the average diameter of the target lumen, into which the endoscope is inserted. For example, the average diameter of the upper gastrointestinal tract lumen may be different from the average diameter of the lumen of the lower gastrointestinal tract or of other body lumens. As such, the length of the plurality of struts 46 may be adjusted such that in the insertion position, the distal ends of the struts 46 may engage effectively with the lumen without applying an undesirable amount of pressure to the lumen.

Webbing 48, struts 46, and base 44 may be made of the same material or different materials. Suitable materials include thermosets (e.g., rubber or silicone rubber), thermoplastic elastomers (e.g., thermoplastic polyurethane or SANTOPRENE brand thermoplastic vulcanizate, available from Exxon Corporation, Irving, Tex., USA), or other suitable biocompatible materials. Webbing 48 may also be made of thermoplastic polyurethane film, any suitable polymer, or any suitable biocompatible materials. One or more of webbing 48, struts 46, or base 44 may also include a suitable coating, e.g., a lubricious or anti-bacterial coating.

Similarly, flexible arms 34 and base 32 of the dimension-compensating component 30 may be made of the same material or different materials. Suitable materials include hard plastic (e.g., polycarbonate), thermoplastic elastomers (e.g., thermoplastic polyurethane or SANTOPRENE), or other suitable biocompatible materials. One or more of flexible arms 34 or base 32 may also include a suitable coating, e.g., a lubricious or anti-bacterial coating.

Figure 5A:
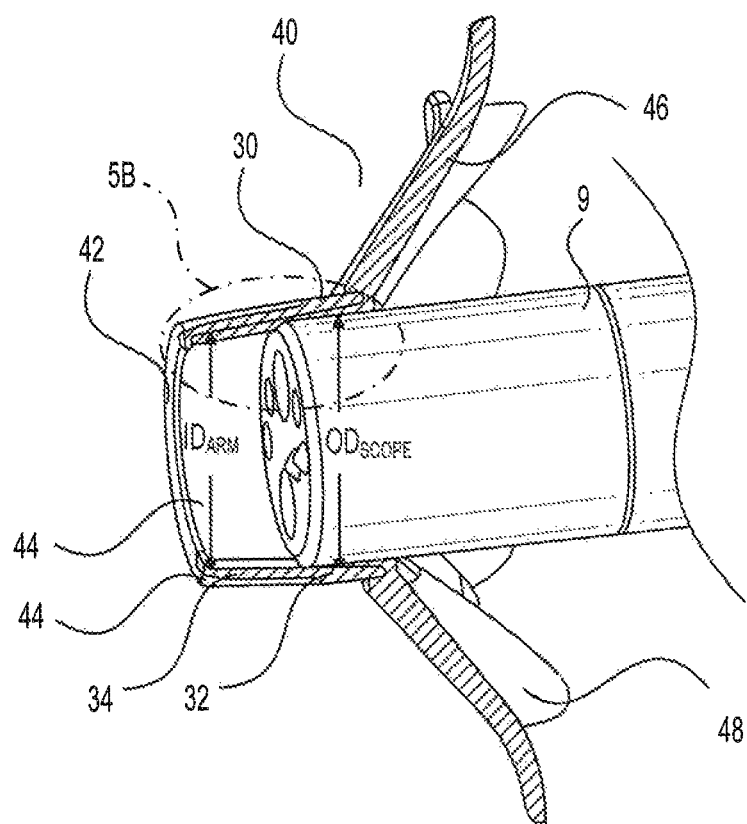
FIGS. 5A-5B illustrate an exemplary endoscope accessory assembly mounted on an endoscope tip.
Figure 5B:
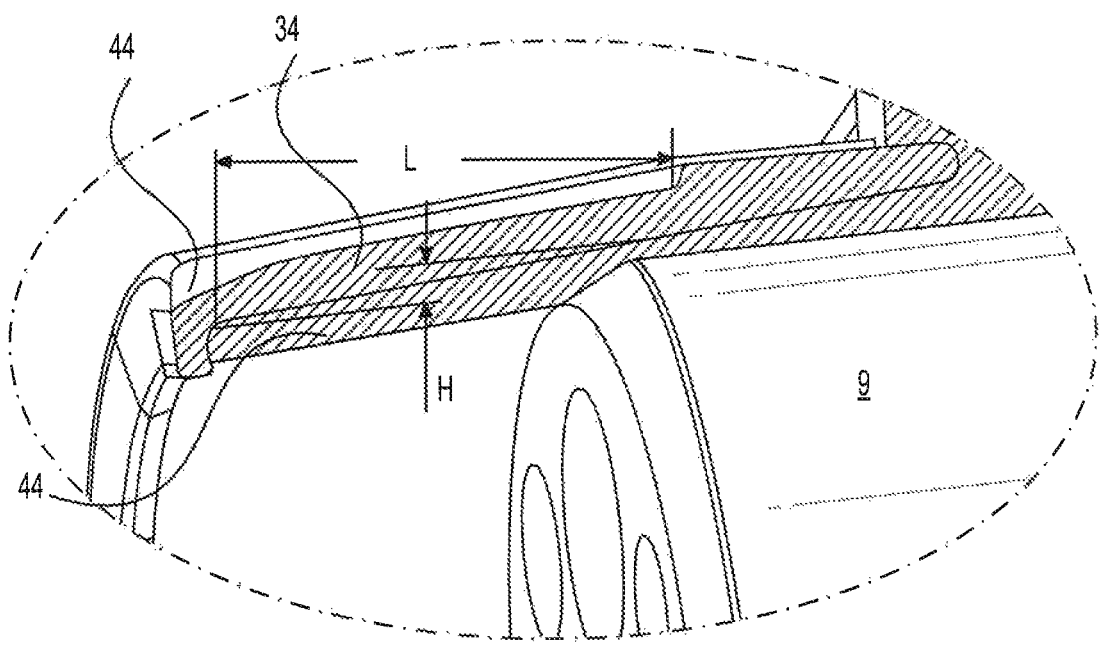

Reference is now made to FIGS. 5A-5B, which illustrate an exemplary endoscope accessory assembly 40 mounted on an endoscope tip 9. FIG. 5B illustrates an expanded view of section "5B" in FIG. 5A. The exemplary endoscope accessory assembly 40 in FIGS. 5A and 5B comprise an accessory device 42 over-molded onto the dimension-compensating component 30. Once over-molded, the inner diameter at a distal end of the flexible arms 34 ($ID_{ARM}$) may be smaller than the outer diameter of the endoscope tip 9 ($ID_{SCOPE}$). When the assembly 40 attaches to the endoscope tip 9, the flexible arms 34 may deform outward and generate a force inward onto the endoscope tip 9. This is called the attachment and detachment force. The force generated by one of the plurality of flexible arms 34 may be expressed using the following equation:

$$F = K \times 3 \times E \times I \times \frac{H}{L^3}$$

where K is the coefficient of friction;

E is the modulus of elasticity of the base 32 of the dimension-compensating component 30;

I is the moment of inertia of the cross-section of the arm 34;

H is the deformation of the arm 34 (also referred to as an amount of interference); and L is the length of the arm 34.

The deformation (H) of the arm 34 can also be expressed as half of the difference between the outer diameter of the endoscope tip 9 and the inner diameter at a distal end of the flexible arms 34.

$$H = \frac{OD_{SCOPE} - ID_{ARM}}{2}$$

All of the variables of the force equation remain constant, except for the $ID_{ARM}$ and consequently, deformation (H) of the arm 34. The $ID_{ARM}$ of the arm 34 may vary within a specified manufacturing tolerance. Accordingly, the force generated may also vary because the force generated becomes a function of the arm inner diameter at rest $ID_{ARM}$ and/or amount of interference of the arm 34. For example, if the inner diameter of the arm is set at 2 mm smaller than the outer diameter of the scope, and manufacturing tolerance of the inner diameter is set to +/−0.2 mm, the interference would vary within 1±0.1 mm (20%), the attachment and detachment force would also vary proportionately within 20%. This makes this dimension-compensating component less sensitive to the dimensional variation than the crush rib. In addition, because the direction of the deformation (H) of the arm 34 is inward, it is not necessary to change the outside diameter of the assembly 40 to change the interference force as it is needed with the crush ribs. Instead, the diameter of the base 44 may remain constant, and only the inner diameter at the distal end of the flexible arms 34 ($ID_{ARM}$) may vary via deformation of the arms 34.

Figure 6A:
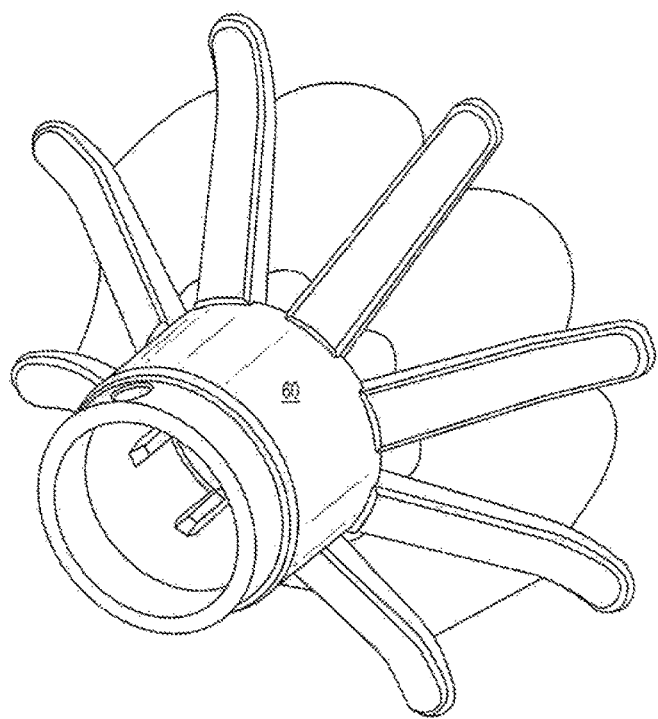
FIGS. 6A-6B illustrate a straight extension cup and a prior accessory device coupled to the straight extension cup.
Figure 6B:
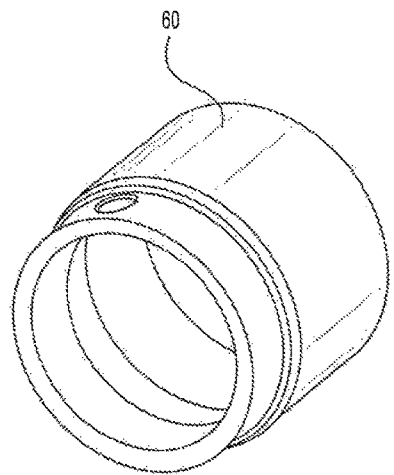

As mentioned previously, in order to ensure the endoscope accessory assembly 40 does not easily disengage with the endoscope tip 9 and to ensure the endoscope tip 9 is not damaged during removal of the assembly 40, the attachment and detachment force would generally need to be between about 3 and 5 lbs. Accordingly, the flexible arms 34 of the dimension-compensating component 30 may be configured to deform outward sufficiently in order to generate about 3 to 5 lbs. of force. For example, the arms 34 may be configured to deform within a range of about 1.0 mm. In some embodiments, the flexible arms 34 may deform within a range of about 0.2 mm or about 0.5 mm, or about 2 mm depending on the geometry (cross-section and length) and material of the arms 34. Reference is now made to FIGS. 6A and 6B, which illustrate a straight extension cup and a prior accessory device coupled to the straight extension cup. The base of the prior accessory device further comprises a distal extension cup 60. The extension cup 60 may increase the sliding friction and may further prevent the endoscope accessory assembly from falling off an endoscope tip (not shown) during a procedure. Further, in extending beyond a distal end of the endoscope tip, the extension cup 60 may aid in holding back the body lumen such that a camera at the distal end of the endoscope tip has an unobstructed view. The inner diameter of the extension cup may be dimensioned to receive a distal end of the endoscope tip. In some embodiments, the extension cup 60 may further comprise one or more crushed ribs on an inner surface of the extension cup 60.

Figure 7A:
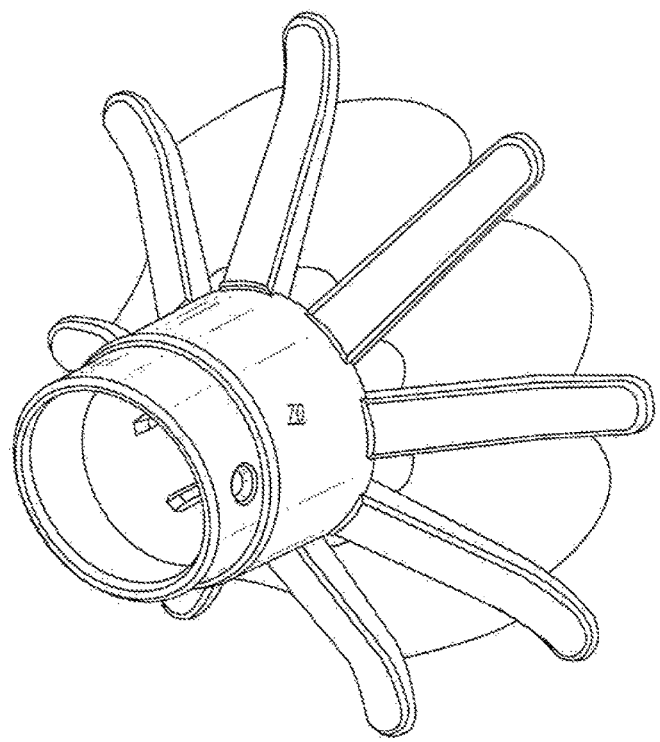
Figure 7B:
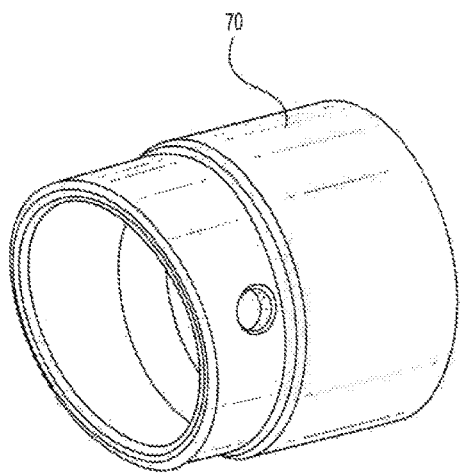

Reference is now made to FIGS. 7A and 7B, which illustrate a tilted extension cup and a prior accessory device coupled to the tilted extension cup. The tilted extension cup 70 is similar to the straight extension cup 60 of FIG. 6. However, the tilted extension cup 70 further comprises a distal end that is tilted at an angle relative to a vertical axis. In some embodiments, the extension cup 70 may be tilted at an angle from about 5° to about 45°. Similar to the extension cup 60 of FIG. 6, the tilted extension cup 70 may increase the sliding friction, and may aid in holding back the body lumen such that a camera at the distal end of the endoscope tip has an unobstructed view. The tilted extension cup 70 may also comprise one or more crushed ribs on an inner surface of the extension cup 70.

Figure 8A:
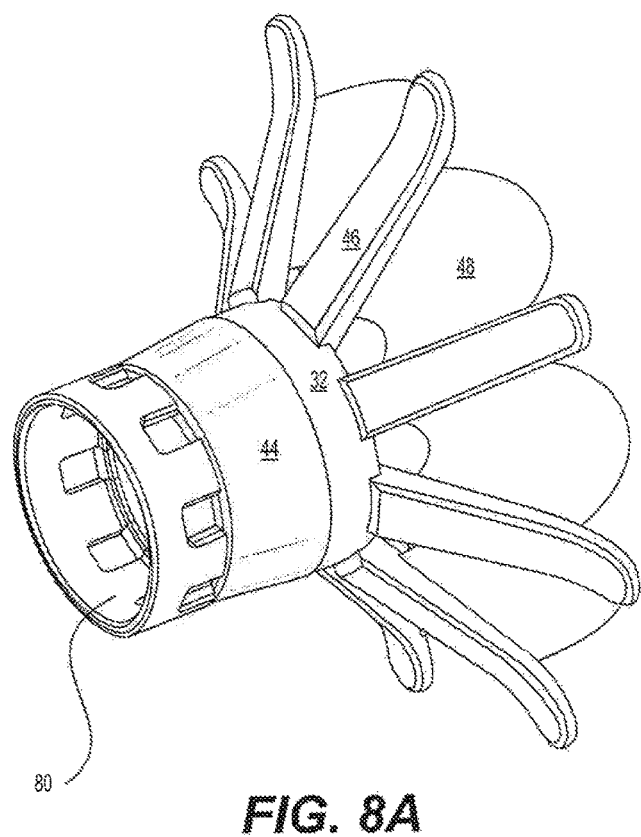
FIGS. 8A-8B illustrate an exemplary straight extension cup and an exemplary endoscope accessory assembly coupled to the exemplary straight extension cup, in accordance with an embodiment of the present disclosure.
Figure 8B:
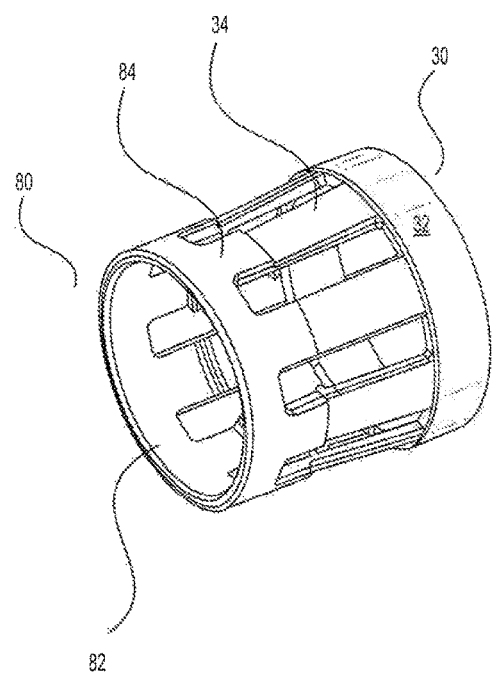

In other embodiments, the extension cups 60 and 70 may be redesigned based on the exemplary endoscope accessory assembly 40 of the present disclosure. Reference is now made to FIGS. 8A and 8B, which illustrate an exemplary straight extension cup and an exemplary endoscope accessory assembly coupled to the exemplary straight extension cup, in accordance with an embodiment of the present disclosure. The exemplary straight extension cup 80 comprises a base 82 and a plurality of arms 84. The plurality of arms 84 may be straight such that the inner diameter along the length of the arms 84 remains constant throughout. Accordingly, the inner diameter at a distal end of the arms 84 may be equivalent to the inner diameter at the base 82.

In some embodiments, the plurality of arms 84 of the extension cup 80 may be configured to removably couple to the plurality of flexible arms 34 of the dimension-compensating component 30. The plurality of arms 84 may be coupled to the flexible arms 34 by an adhesive, glue, epoxy, or any other suitable and biocompatible means. The plurality of arms 84 may, also, be flexible or rigid. At least a portion of the plurality of arms 84 and the base 82 may be configured to extend beyond a distal end of the base 44 of the accessory device 42 when the accessory device 42 is over-molded onto the dimension-compensating component 30.

The extension cup 80 may be formed of any suitable material. Suitable materials could include plastic (e.g., polycarbonate), thermosets (e.g., rubber or silicone rubber), thermoplastic elastomers (e.g., thermoplastic polyurethane or SANTOPRENE), or other suitable biocompatible materials. As mentioned previously, the extension cup 80 may increase the sliding friction between the endoscope accessory assembly 40 and the endoscope tip (not shown), and may further prevent the endoscope accessory assembly 40 from falling off an endoscope tip during a procedure. Further, in extending beyond a distal end of the endoscope tip, the extension cup 80 may aid in holding back the body lumen such that a camera at the distal end of the endoscope tip has an unobstructed view.

Figure 9A:
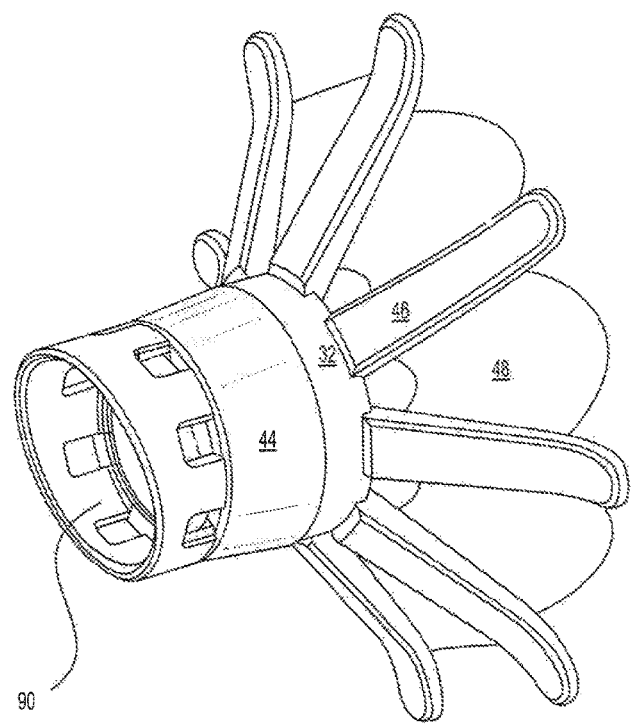
FIGS. 9A-9B illustrate an exemplary tilted extension cup and an exemplary endoscope accessory assembly coupled to the exemplary tilted extension cup, in accordance with an embodiment of the present disclosure.
Figure 9B:
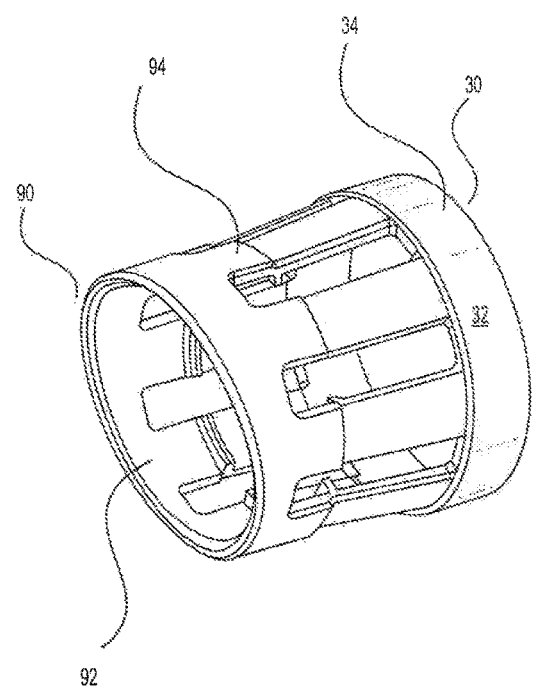

Reference is now made to FIGS. 9A and 9B, which illustrate an exemplary tilted extension cup and an exemplary endoscope accessory assembly coupled to the exemplary straight extension cup, in accordance with an embodiment of the present disclosure. The exemplary straight extension cup 90 comprises a base 92 and a plurality of arms 94. The plurality of arms 94 may be straight such that the inner diameter along the length of the arms 94 remains constant throughout. Accordingly, the inner diameter at a distal end of the arms 94 may be equivalent to the inner diameter at the base 92.

In some embodiments, the plurality of arms 94 of the extension cup 90 may be configured to removably couple to the plurality of flexible arms 34 of the dimension-compensating component 30. The plurality of arms 94 may be coupled to the flexible arms 94 by an adhesive, glue, epoxy, or any other suitable and biocompatible means. The plurality of arms 94 may, also, be flexible or rigid. At least a portion of the plurality of arms 94 and the base 82 may be configured to extend beyond a distal end of the base 44 of the accessory device 42 when the accessory device 42 is over-molded onto the dimension-compensating component 30.

The extension cup 90 may be formed of any suitable material. Suitable materials could include plastic (e.g., polycarbonate), thermosets (e.g., rubber or silicone rubber), thermoplastic elastomers (e.g., thermoplastic polyurethane or SANTOPRENE), or other suitable biocompatible materials. As mentioned previously, the extension cup 90 may increase the sliding friction between the endoscope accessory assembly 40 and the endoscope tip (not shown), and may further prevent the endoscope accessory assembly 40 from falling off an endoscope tip during a procedure. Further, in extending beyond a distal end of the endoscope tip, the extension cup 90 may aid in holding back the body lumen such that a camera at the distal end of the endoscope tip has an unobstructed view.

The main difference between the extension cup 90 and the extension cup 80 of FIG. 8 may be the distal end of the base 92 and 82. The base 82 of the extension cup 80 in FIG. 8 may be straight, whereas the base 92 of the extension cup 92 may be tilted at an angle relative to a vertical axis. In some embodiments, the extension cup 90 may be tilted at an angle from about 5° to about 45° relative to a vertical axis.

While the present disclosure is described herein with reference to illustrative embodiments of endoscope attachments used for particular applications, such as for performing medical procedures, it should be understood that the embodiments described herein are not limited thereto. For example, scopes and similar devices are often used in industrial applications, e.g., to inspect and/or repair machinery. Endoscope attachments of the present disclosure may also be used with industrial scopes in non-medical settings. Those having ordinary skill in the art and access to the teachings provided herein will recognize additional modifications, applications, embodiments, and substitution of equivalents that all fall within the scope of the disclosed embodiments. Accordingly, the disclosed embodiments are not to be considered as limited by the foregoing or following descriptions.

The many features and advantages of the present disclosure are apparent from the detailed specification, and thus it is intended by the appended claims to cover all such features and advantages of the present disclosure that fall within the true spirit and scope of the present disclosure. Further, since numerous modifications and variations will readily occur to those skilled in the art, it is not desired to limit the present disclosure to the exact construction and operation illustrated and described and accordingly, all suitable modifications and equivalents may be resorted to, falling within the scope of the present disclosure.

Moreover, those skilled in the art will appreciate that the conception upon which this disclosure is based may readily be used as a basis for designing other structures, methods, and systems for carrying out the several purposes of the present disclosure. Accordingly, the claims are not to be considered as limited by the foregoing description.

What is claimed is:

1. An endoscope accessory assembly, comprising:
an accessory device, further comprising:
a first base having a first inner surface dimensioned to receive a distal end of an endoscope,
a plurality of flexible struts extending radially out from the first base in a first direction, and
webbing connecting each of the flexible struts and configured to form a collapsible umbrella;
a dimension-compensating component, further comprising:
a second base having a second inner surface dimensioned to receive at least a portion of an outer surface of the first base,
a plurality of flexible arms extending radially out from the second base in a second direction opposite the first direction, and
at least one projection extending radially inward at a distal end of the arms,
wherein the accessory device is over-molded onto the dimension-compensating component such that the first base of the accessory device completely encapsulates the plurality of flexible arms of the dimension-compensating component while the second base is exposed.

2. The endoscope accessory assembly of claim 1, wherein at least one of the first base or the second base is triangular, rectangular, or cylindrical in shape.

3. The endoscope accessory assembly of claim 1, wherein the at least one projection is configured to stop the distal end of the endoscope from extending beyond the distal end of the arms.

4. The endoscope accessory assembly of claim 1, wherein an inner diameter at a distal end of the arms is less than an outer diameter of the distal end of the endoscope.

5. The endoscope accessory assembly of claim 1, wherein the flexible arms deform inward at rest such that an inner diameter of the second base is greater than an inner diameter at the distal end of the arms.

6. The endoscope accessory assembly of claim 5, wherein:
the plurality of flexible arms is configured to deform outward when the accessory device receives the distal end of the endoscope; and
the plurality of flexible arms is configured to generate a force inward onto the distal end of the endoscope.

7. The endoscope accessory assembly of claim 1, wherein an inner diameter of the first base remains constant.

8. The endoscope accessory assembly of claim 1, wherein:
the dimension-compensating component is made of plastic, and
the accessory device is made of silicone.

9. The endoscope accessory assembly of claim 1, wherein the first inner surface of the accessory device comprises at least one crush rib.

10. The endoscope accessory assembly of claim 1, further comprising an extension cup coupled to the distal end of the flexible arms such that, when the accessory device is over-molded onto the dimension-compensating component, the extension cup extends beyond a distal end of the first base.

11. The endoscope accessory assembly of claim 10, wherein the extension cup further comprises:
a third base; and
a second plurality of flexible arms configured to couple to the distal end of the flexible arms of the dimension-compensating component.

12. The endoscope accessory assembly of claim 11, wherein a distal end of the third base is tilted at an angle along a vertical axis.

* * * * *